(12) United States Patent
Khayal et al.

(10) Patent No.: US 7,442,187 B2
(45) Date of Patent: Oct. 28, 2008

(54) MULTIPLE NEEDLE INJECTION CATHETER

(75) Inventors: Inas Khayal, San Francisco, CA (US);
Wendy Naimark, Cambridge, MA (US);
Maria Palasis, Wellesley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 103 days.

(21) Appl. No.: 11/051,638

(22) Filed: Jan. 27, 2005

(65) Prior Publication Data

US 2006/0167418 A1    Jul. 27, 2006

(51) Int. Cl.
A61M 5/178    (2006.01)
(52) U.S. Cl. .................................................. 604/164.11
(58) Field of Classification Search ............ 604/164.11, 604/264, 93.01, 110, 28, 117, 891.1, 57; 606/167, 170; 623/1.11; 424/422, 424
See application file for complete search history.

(56) References Cited

U.S. PATENT DOCUMENTS

| | | | |
|---|---|---|---|
| 3,492,992 A | | 2/1970 | Kurtz |
| 4,411,655 A | * | 10/1983 | Schreck ................. 604/165.01 |
| 4,578,061 A | | 3/1986 | Lemelson |
| 4,735,611 A | | 4/1988 | Anderson et al. |
| 4,790,817 A | | 12/1988 | Luther |
| 4,791,937 A | | 12/1988 | Wang |
| 4,824,433 A | | 4/1989 | Marz et al. |
| 4,861,341 A | | 8/1989 | Woodburn |
| 4,900,303 A | * | 2/1990 | Lemelson ................... 604/514 |
| 4,966,586 A | | 10/1990 | Vaillancourt |
| 5,085,631 A | * | 2/1992 | Leighton ..................... 604/28 |
| 5,306,239 A | | 4/1994 | Gurmarnik et al. |
| 5,364,373 A | | 11/1994 | Waskonig et al. |
| 5,630,802 A | | 5/1997 | Moellmann et al. |
| 6,004,302 A | | 12/1999 | Brierly |
| 6,077,248 A | | 6/2000 | Zumschlinge |
| 6,203,532 B1 | | 3/2001 | Wright |
| 6,238,406 B1 | * | 5/2001 | Ellis et al. .................... 606/167 |
| 6,379,333 B1 | * | 4/2002 | Brimhall et al. ........ 604/164.11 |
| 6,488,659 B1 | | 12/2002 | Rosenman |

(Continued)

FOREIGN PATENT DOCUMENTS

GB    1 284 537    8/1972

(Continued)

*Primary Examiner*—Nicholas D. Lucchesi
*Assistant Examiner*—Christopher D Koharski
(74) *Attorney, Agent, or Firm*—Vidas, Arrett & Steinkraus

(57) ABSTRACT

Embodiments of the present invention relate to multiple needle catheter-based injection systems to deliver a plug of a therapeutic or other agent. A medical device may include a catheter with a distal end, a proximal end and a catheter lumen extending therebetween and an outer needle disposed in the catheter lumen with a distal end and a proximal end and an outer needle lumen extending therebetween. The medical device may include an inner needle with a distal end and a proximal end, the inner needle being disposed in the outer needle lumen and the distal end of the inner needle to receive and hold a therapeutic plug, and a needle control mechanism coupled to the proximal ends of the outer needle and the inner needle, the needle control mechanism to independently and jointly control ejection and retraction of the outer and inner needles to deliver the therapeutic plug into a target tissue site.

20 Claims, 7 Drawing Sheets

U.S. PATENT DOCUMENTS

| | | | |
|---|---|---|---|
| 6,491,670 B1 | 12/2002 | Toth et al. | |
| 6,530,902 B1 | 3/2003 | Jonkman | |
| 6,547,787 B1 | 4/2003 | Altman et al. | |
| 6,641,564 B1 | 11/2003 | Kraus | |
| 6,733,515 B1 | 5/2004 | Edwards et al. | |
| 6,786,929 B2* | 9/2004 | Gambale et al. | 623/11.11 |
| 7,070,582 B2* | 7/2006 | Freyman et al. | 604/272 |
| 2002/0111603 A1 | 8/2002 | Cheikh | |
| 2002/0177864 A1 | 11/2002 | Camrud | |
| 2003/0105436 A1* | 6/2003 | Ponzi | 604/264 |
| 2003/0158519 A1 | 8/2003 | Epstein et al. | |
| 2004/0030282 A1 | 2/2004 | Epstein et al. | |
| 2004/0082906 A1 | 4/2004 | Tallarida | |
| 2004/0116856 A1 | 6/2004 | Woehr et al. | |
| 2004/0122349 A1* | 6/2004 | Lafontaine et al. | 604/11 |
| 2004/0204672 A1 | 10/2004 | Palasis et al. | |

FOREIGN PATENT DOCUMENTS

| | | |
|---|---|---|
| WO | WO 01/62141 | 8/2001 |

\* cited by examiner

MULTIPLE NEEDLE INJECTION CATHETER

FIELD OF THE INVENTION

Embodiments of the present invention relate to catheters and methods for the injection of therapeutic and other agents at a target site within a patient's body. More particularly, the embodiments relate to catheter-based injection systems with multiple needles to deliver a plug of a therapeutic or other agent.

BACKGROUND

Medical catheters are used for innumerable minimally invasive medical procedures. Catheters, specifically, injection catheters, may be used, for example, for delivery of therapeutic drug doses to target tissue and/or for delivery of medical devices such as lumen-reinforcing or drug-eluting stents. Likewise, catheters may be used to guide medical instruments to a target site to perform a surgical procedure, such as tissue rescission, ablation of obstructive deposits or myocardial revascularization.

Currently, injection-catheter-based systems include catheters with and without sensors. Injection-catheters without sensors have an opening at the distal end of the catheter to permit a needle or a medical device to pass through the opening and into a target tissue site in the patient. Injection-catheters that are equipped with sensors (for example, electrodes) have a sensor tip at the distal end of the catheter with an opening to permit a needle or a medical device to pass through the opening and into target tissue in the patient. The sensor systems usually have one or more additional return sensors implemented as bands circumferentially around the catheter. In some systems, tissue contact is determined by measuring the impedance between the tip sensor when it is in contact with tissue and a return sensor that is not in contact with the tissue but is only in contact with a fluid, for example, blood, that is surrounding the tissue. However, this determination is based on known, that is, pre-determined, impedance values when the electrode is in contact with tissue and when only in contact with body fluids (for example, blood).

Likewise, needles used with injection-catheters currently work by positioning the device over tissue at the injection site, pushing the needle out of the catheter and into the tissue, delivering a therapeutic agent into the tissue, and retracting the needle. However, this usually results in the loss of some of the therapeutic agent from the tissue when the needle is withdrawn, which can not only diminish the effectiveness of the injected therapeutic agent, but also cause adverse side-effects due to the lost therapeutic agent travelling to undesirable locations within the patient. The local delivery of therapeutic agents to heart-wall and coronary arteries has shown promise in treating heart disease. These agents include gene therapies, drugs, proteins, extracellular matrices, and cells. Localized delivery is important due to potential adverse effects associated with systemic delivery of the therapy and the therapeutic benefit of a concentrated dose delivered to the affected site. Unfortunately, current injection-catheters do not enable the optimal targeted delivery of therapeutic agents to provide the most effective treatment regimen, since the tissue in which the therapeutic agent is delivered does not always retain all of the injected therapeutic.

SUMMARY OF THE INVENTION

The invention is directed to improved multiple needle injection-catheter systems with and without sensors and the related methods for delivering therapeutics therewith. In certain embodiments, a device and method are provided for injecting a therapeutic plug at a target site within a patient's body. In other embodiments, a device and method are provided for injecting the therapeutic plug and other fluids at the target site within a patient's body. The device may include a catheter with a distal end and a proximal end and a catheter lumen extending there between; and an outer needle with a distal end and a proximal end and an outer needle lumen extending there between, the outer lumen being disposed in the catheter lumen. The device may also include an inner needle with a distal end and a proximal end, the inner needle being disposed in the outer needle lumen and the distal end of the inner needle to receive and hold a therapeutic plug. The device may further include a needle control mechanism coupled to the proximal ends of the outer needle and the inner needle, the needle control mechanism to control the independent and joint ejection and retraction of the outer and inner needles to deliver the therapeutic plug into a target tissue site.

Other aspects of the invention are set forth in the appended claims.

BRIEF DESCRIPTION OF THE DRAWINGS

The foregoing and further features and advantages of the invention will become apparent from the following description of preferred embodiments with reference to the accompanying drawings, wherein like numerals are used to represent like elements and wherein.

DETAILED DESCRIPTION

Some embodiments of the present invention may include a needle-based direct injection device similar to, for example, a Stiletto catheter manufactured by Boston Scientific of Natick, Mass., with or without an electrode sensor tip. In some embodiments, the sensor tip may include at least two electrodes separated by an insulator and connected to a monitoring device, for example, an electrocardiogram (EKG) to permit the monitoring of electrical signals in tissue that is in contact with the electrodes. For example, if the sensor tip were placed at a specific location (e.g., the pulmonary veins, left ventricle and AV node of the heart), the sensor tip may read any distinct electrical patterns generated by the tissue. Therefore, the sensor tip may be used to locate a characteristic electrical pattern known to be associated with a specific tissue location and target the location for the injection of therapeutics.

It is believed that injecting certain therapeutic agents, for example, certain genetic substances, into the pulmonary veins, left ventricle and AV node of the heart may provide a superior treatment for certain arrhythmias, such as, bradyarrhythmia and ventricular tachyarrhythmia. Unfortunately, current treatments, for example, oral drugs, radio frequency ablation, and implantable devices lack the desired effectiveness and have undesirable side effects. Fortunately, direct injection of a therapeutic agent, for example, a gene therapy agent, into the target tissue may provide a significantly improved effectiveness and with fewer side effects.

Figure 1:
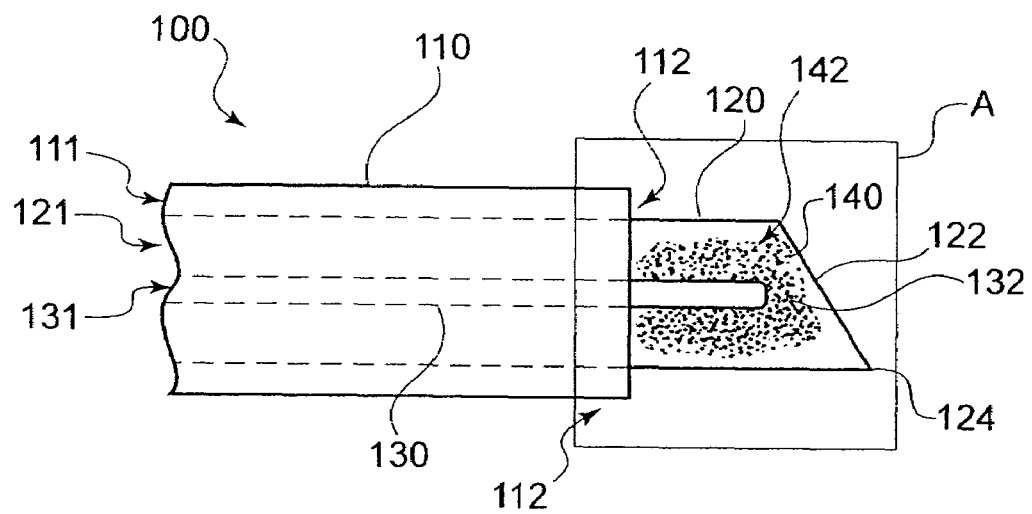
FIG. 1 is a partial cross-sectional side view of the distal end of a catheter, in accordance with an embodiment of the present invention.

FIG. 1 is a partial cross-sectional side view of the distal end of a catheter, in accordance with an embodiment of the present invention. In FIG. 1, a multiple needle catheter system 100 may include a catheter 110, an outer needle 120 disposed within catheter 110, an inner needle 130 disposed within outer needle 120 and a plug 140 attached to and substantially covering a distal end 132 of inner needle 130. Catheter 110 may have a catheter proximal end 111 and a catheter distal end 112 and a lumen (not shown) extending between catheter proximal end 111 and catheter distal end 112 through which outer needle 120, inner needle 130 and plug 140 may travel. Outer needle 120 may have an outer needle proximal end 121 and an outer needle distal end 122 and an outer needle lumen (not shown) extending between outer needle proximal end 121 and outer needle distal end 122 through which inner needle 130 and plug 140 may travel. Outer needle 120 may also have a pointed tip 124 to puncture a target tissue site to permit the injection of inner needle 130 and plug 140 into the target tissue site. Similarly, inner needle 130 may also have an inner needle proximal end 131 and an inner needle distal end 132, where inner needle distal end 132 may be rounded and/or blunted to prevent inner needle 130 from poking through plug 140 and into the target tissue site and potentially injuring a patient and/or making it harder to deposit plug 140 in the target tissue site. Inner needle 130 may also include a shape memory material, for example, nitinol and polymers such as block copolymers of caprolactone and dioxanone that may contract when exposed to body temperatures. As a result of the contraction of the shape memory material, inner needle 130 may separate from plug 140, thus making the removal of inner needle 130 easier.

In general, in FIG. 1, the diameter of the outer needle lumen of outer needle 120 may be significantly larger than an outer diameter of inner needle 130 to permit inner needle 130 and plug 140 to both travel through the inner lumen of outer needle 120 when plug 140 is covering distal end 132 of inner needle 130. The distance between the outer needle lumen of outer needle 120 and an exterior surface 142 of plug 140 may need to vary to accommodate the size and tackiness of different plugs 140. As a result, inner needle 130 may be easily inserted into and removed from outer needle 120, which may permit inner needle 130 to be inserted into outer needle 120 after catheter 110 has been inserted into a patient's body. In fact, inner needle 130 may be inserted into outer needle 120 after outer needle 120 has been ejected into the target tissue site and then removed from outer needle 120 after delivering the plug to the target tissue site. This may enable the repositioning of catheter 110 within the patient's body to introduce additional plugs 140 on new inner needles 130 into the target tissue site without having to remove catheter 110.

In FIG. 1, plug 140 may have a low profile that upon injection into tissue may activate and swell and/or expand against the tissue. The swelling and/or expansion of plug 140 may help to hold plug 140 in the tissue while inner needle 130 may be retracted back into outer needle 120. Alternatively, plug 140 may have a higher affinity for the tissue than for inner needle 130 so that when inner needle 130 is retracted out of plug 140 back into outer needle 120, plug 140 may remain in the tissue.

In accordance with another embodiment of the present invention, catheter 110 of FIG. 1 may include multiple outer needles 120 with associated inner needles 130 to enable the delivery of multiple plugs. The multiple plugs may be delivered either at substantially the same time or in series, as determined by a doctor in accordance with the applicable therapy regime being used.

In accordance with another embodiment of the present invention, inner needle 130 of FIG. 1 may also have an inner needle lumen (not shown) that may extend between the inner needle proximal end and inner needle distal end 132 through which a fluid may travel and an inner needle opening (not shown) defined by inner needle distal end 132 to eject the fluid. For example, the fluid may include a therapeutic agent, a cell therapy, a crosslinker, a second component of a two-component system to create a solid plug in vivo when the plug includes a first component of the two-component system, gene therapies, drugs, proteins, and extracellualar matrices. In general, inner needle distal end 132 may include a blunted end to prevent inner needle 130 from poking through plug 140 and into the target tissue site and potentially injuring the patient and making it harder to deposit plug 140 in the target tissue site.

Figure 2:
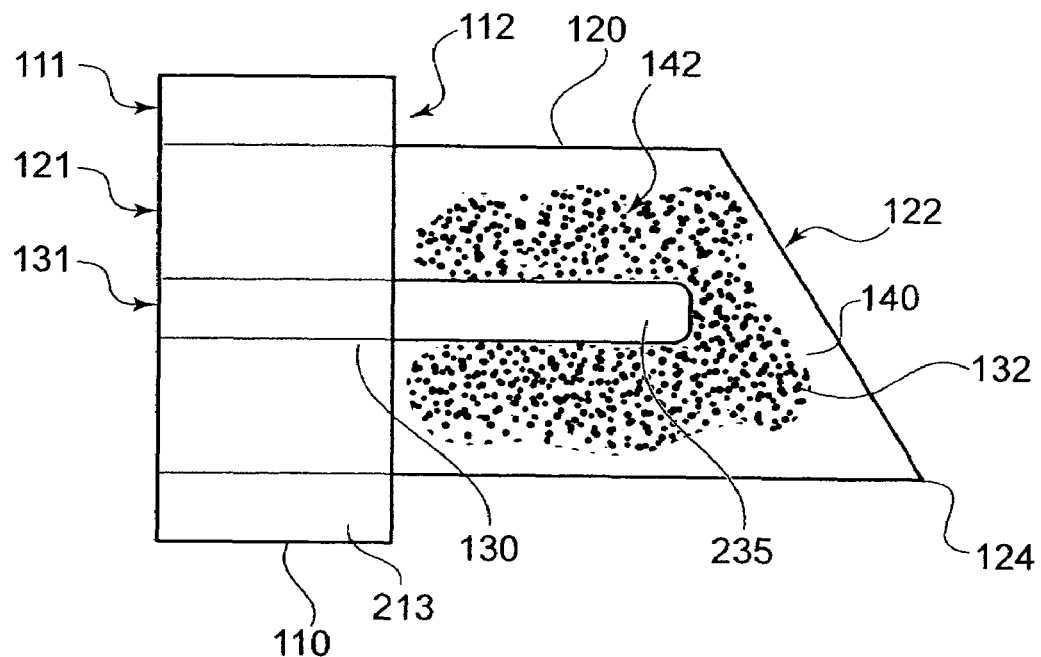
FIG. 2 is an enlarged cross-sectional side view of the distal end of the catheter of FIG. 1 as indicated by box A, in accordance with an embodiment of the present invention.

FIG. 2 is an enlarged longitudinal cross-sectional side view of the distal end of the catheter of FIG. 1 as indicated by plane A, in accordance with an embodiment of the present invention. In FIG. 2, inner needle 130 may include an inner surface 235, which may be flat, if inner needle 130 is solid, or concave, if inner needle 130 has an inner needle lumen. In addition, if inner needle 130 has the inner needle lumen, a distal end of inner needle lumen may define a distal opening that may be in fluid communication with a proximal opening that may be defined by the proximal end of inner needle 130. The distal opening may permit the injection of fluid, for example, therapeutics, drugs, etc., into plug 140 either pre- or post-implant injection of plug 140 into the tissue. Outer needle 120 may include an outer needle lumen 213 that extends from outer needle distal end 122 to outer needle proximal end 121 to permit the introduction of inner needle 130 and plug 140 into an opening in outer needle proximal end 121, passage through outer needle lumen 213, ejection out of an opening in outer needle distal end 122, and withdrawal/retraction of inner needle 130 along the reverse path.

Figure 3:
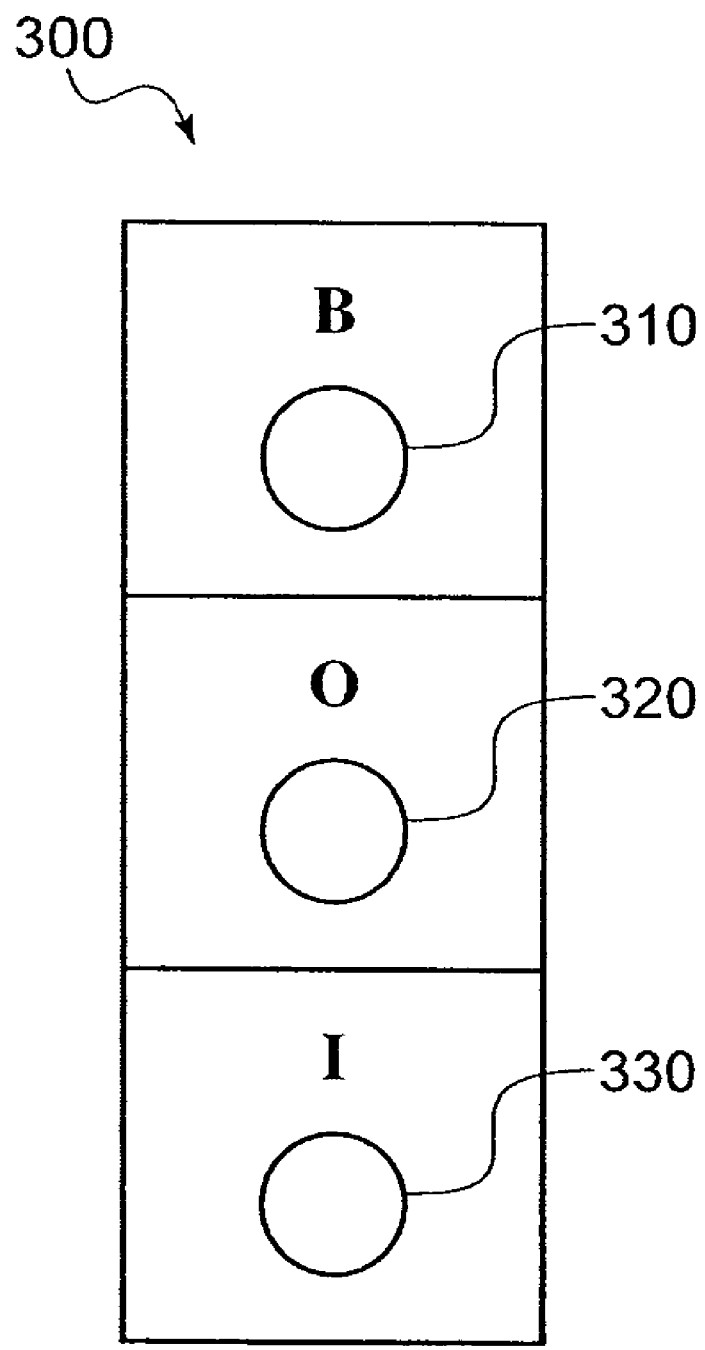
FIG. 3 is a block diagram representation of a method of injecting a plug into a tissue using a multiple needle injection catheter, in accordance with an embodiment of the present invention.

FIG. 3 is a block diagram representation of an actuator for a multiple needle injection catheter, in accordance with an embodiment of the present invention. In FIG. 2, an actuator 300 may include multiple buttons, for example, a both-needle actuator button 310, an outer needle actuator button 320 and an inner needle actuator button 330. Both-needle actuator button 310 may be used to eject and retract both outer needle 120 and inner needle 130 at substantially the same time. In general, both-needle actuator button 310 may operate to move both needles 120, 130 in the opposite direction of their position when both-needle actuator button 310 is activated. For example, if outer needle 120 and inner needle 130 are both retracted within catheter 110, actuating (i.e., pressing) both-needle actuator button 310 may cause both needles 120, 130 to be ejected out catheter distal end 112 a specified distance. Actuating both-needle actuator button 310 when both outer needle 120 and inner needle 130 are extended out past catheter distal end 112, may cause both needles 120, 130 to be retracted back into catheter 110. In an alternative embodiment, actuating both-needle actuator button 310 a first time when both outer needle 120 and inner needle 130 are retracted inside catheter distal end 112, may cause outer needle 120 to be ejected past catheter distal end 112 while leaving inner needle retracted within catheter 110. Actuating both-needle actuator button 310 a second time when only outer needle 120 is extended out past catheter distal end 112, may cause inner needle 130 to be ejected out past catheter distal end 112 with outer needle 120. Actuating both-needle actuator button 310 a third time when both outer needle 120 and inner needle 130 are extended out past catheter distal end 112, may cause outer needle 120 to be retracted back into catheter 110 while leaving inner needle extended. Actuating both-needle actuator button 310 a fourth time when only inner needle 130 is extended out past catheter distal end 112 may cause inner needle 130 to be retracted back into catheter 110. While this embodiment may be easy and inexpensive to implement, since it only requires a single actuator button to implement all of the necessary needle movements, it may not represent the ideal solution. This may be the case, since the order of the needle movements would be fixed and would not be able to be varied by a practitioner, which would prevent the practitioner from determining the needles 120, 130 are not in the desired position and retracting both needles 120, 130 without leaving plug 140 in the tissue.

In one embodiment of actuator 300 of FIG. 3, the specified distance may be controlled by a throw length of the both-needle actuator button 310 that may be preset during the manufacture of actuator 300 or adjustable using a needle depth control mechanism (not shown), as is known in the art, that may be located at catheter proximal end 111. The needle depth control mechanism may be attached to either catheter 110 or to actuator 300 to, in general, control the length of the outer needle 120 that may be ejected from/retracted into catheter distal end 112, which, when both needles 120, 130 are ejected together, may also control the length of inner needle 130 that is ejected/retracted. The needle depth control mechanism may also independently control the ejection/retraction distance of both outer needle 120 and inner needle 130. This ability is needed to permit an outer needle actuator button 320 to control the distance outer needle 120 may be ejected from and retracted into catheter 110 independent of inner needle 130. Similarly, this ability is needed to permit an inner needle actuator button 330 to control the distance inner needle 130 may be ejected from and retracted into catheter 110 independent of outer needle 120.

In accordance with another embodiment of the present invention, a single actuator button, for example, both-needle actuator button 310, may be implemented to perform all of the movements of the needles 120, 130 to inject plug 140 into a target tissue, with a single actuation of the single actuator button. Specifically, actuating the single actuator button may cause both needles 120, 130 to be substantially simultaneously ejected out past catheter distal end 112 and into a target tissue site. Outer needle 120 may be automatically retracted back into catheter 110 after both needles 120, 130 are fully ejected out past catheter distal end 112. Inner needle 130 may automatically be retracted back into catheter 110 after outer needle 120 has been retracted into catheter 110. While this embodiment may not be as easy and inexpensive to implement as the manual version of the single actuator button, it likewise may not represent the ideal solution for similar reasons. Specifically, since the order of the needle movements would be fixed and would not be able to be varied by a practitioner, this would again prevent the practitioner from determining the needles 120, 130 are not in the desired position and retracting both needles 120, 130 without leaving plug 140 in the tissue.

Figure 4:
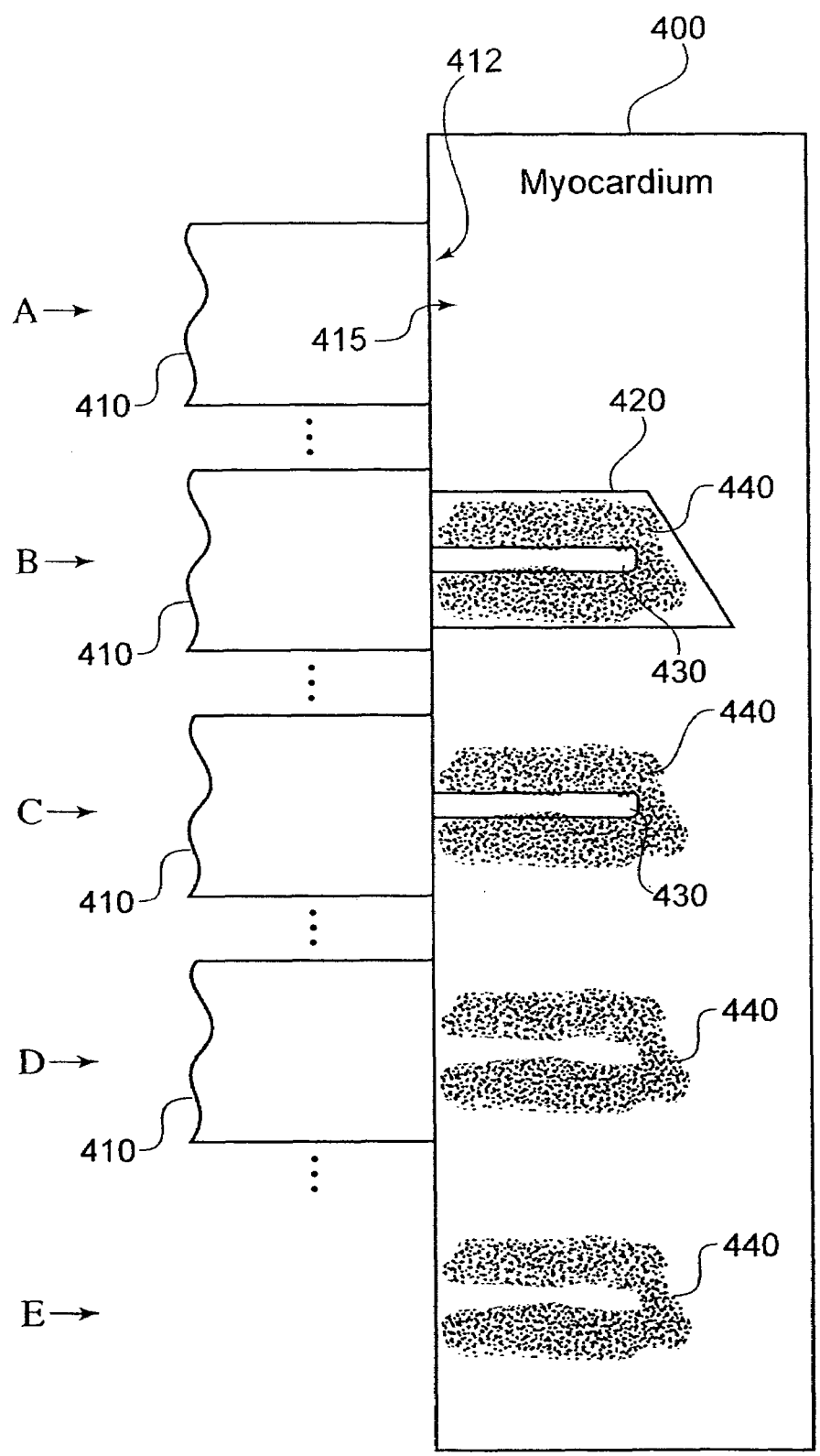
FIG. 4 is a block diagram representation of an actuator for a multiple needle injection catheter, in accordance with an embodiment of the present invention.

FIG. 4 is a block diagram representation of a method of injecting a plug into a tissue, for example, a myocardium tissue section 400, using a multiple needle injection catheter, in accordance with an embodiment of the present invention. In FIG. 4, the method may include positioning (A) a catheter 410 distal end 412 at an injection site 415, for example, a target tissue injection site, in myocardium tissue section 400 so that catheter distal end 412 abuts injection site 415. The method may also include ejecting (B) an outer needle 420 and an inner needle 430 with a plug 440 into injection site 415 either substantially simultaneously or one at a time. In general, outer needle 420 is injected into injection site 415 before inner needle 430 and plug 440, since outer needle 420 has a sharp tip to puncture tissue and needle 430 and plug 440 do not. Specifically, outer needle 420 may be ejected from catheter 410 into injection site 415 separate from or substantially simultaneously with inner needle 430. If outer needle 420 and inner needle 430 are ejected together, inner needle 430 may be recessed within outer needle 420 to permit outer needle 420 to puncture injection site 415. The method may further include retracting (C) outer needle 420 from injection site 415 and back into catheter 410 while leaving inner needle 430 and plug 440 in injection site 415. The method may still further include retracting (D) inner needle 430 from injection site 415 and back into catheter 410 and outer needle 430 while leaving plug 440 in injection site 415. The method may finally include removing (E) catheter 410 from injection site 415 with plug 440 embedded in injection site 415.

Figure 5:
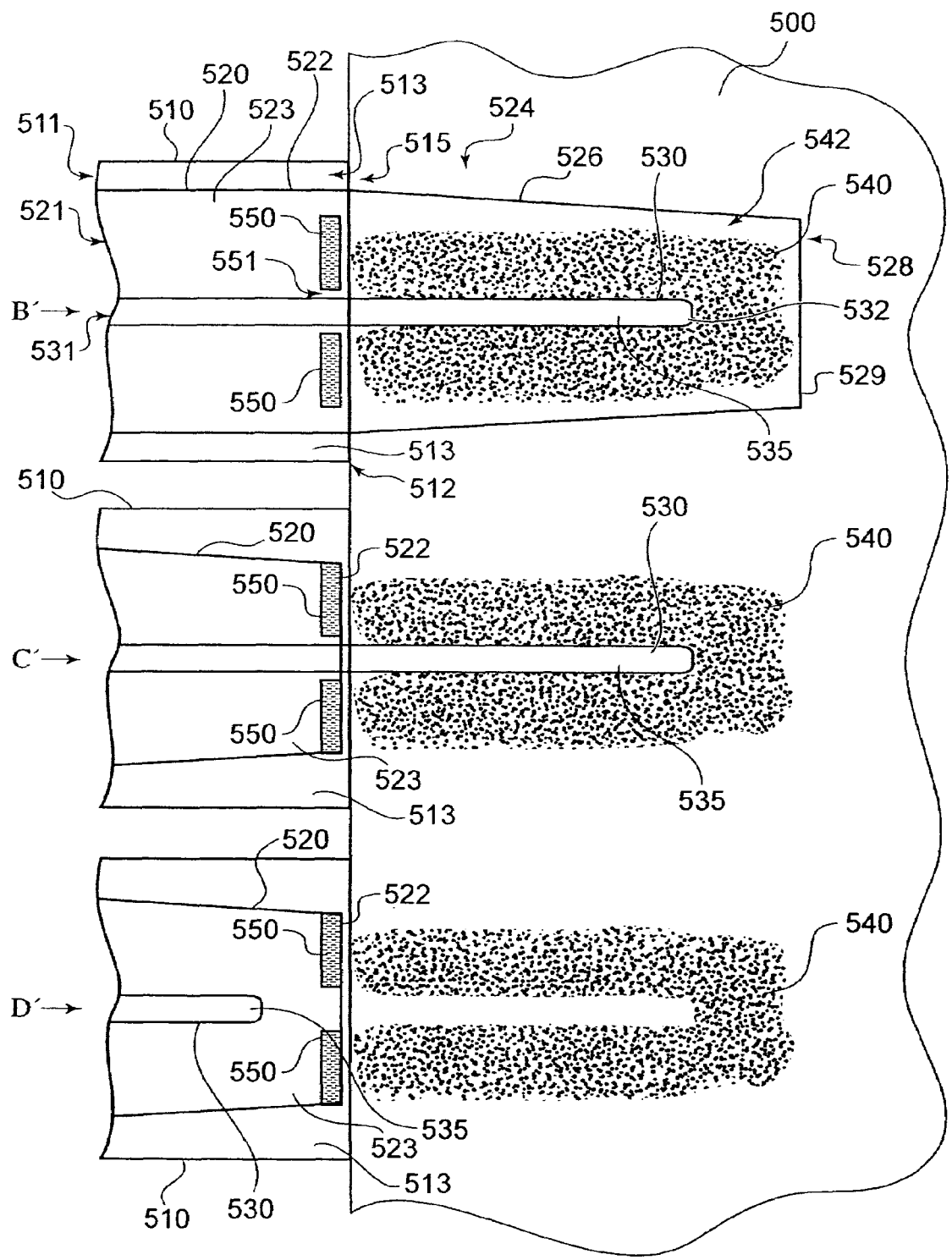
FIG. 5 is a cross-sectional block diagram representation of an alternative portion of the method of injecting a plug into a tissue using a multiple needle injection catheter of FIG. 3, in accordance with another embodiment of the present invention.

FIG. 5 is a cross-sectional block diagram representation of an alternative portion of the method of injecting a plug into a tissue showing the use of an alternative embodiment of a multiple needle injection catheter of FIG. 3, in accordance with another embodiment of the present invention. Specifically, in FIG. 5, the alternative embodiment of a multiple needle injection catheter system 500 may include a catheter 510, an outer needle 520 disposed within catheter 510, an inner needle 530 disposed within outer needle 520 and a plug 540 attached to and substantially covering a distal end 532 of inner needle 530. Catheter 510 may have a catheter proximal end 511 and a catheter distal end 512 and a lumen 513 extending between catheter proximal end 511 and catheter distal end 512 through which outer needle 520, inner needle 530, plug 540 and disk 550 may travel. Outer needle 520 may have an outer needle proximal end 521 and an outer needle distal end 522 and an outer needle lumen 523 extending between outer needle proximal end 521 and outer needle distal end 522 through which inner needle 530 and plug 540 may travel. Outer needle distal end 522 may have a sharp circular tip 524 to puncture a target tissue site to permit the injection of inner needle 530 and plug 540 into the target tissue site. Specifically, tip 524 may include a symmetrically tapered portion defined by a conical-shaped wall 526 attached to outer needle distal end 522 and angling distally and inwardly to form an opening 528. Opening 528 may include a rim 529 with a distally facing cutting edge to cut and penetrate into tissue.

Similarly, in FIG. 5, inner needle 530 may also have an inner needle proximal end 531 and an inner needle distal end 532, where inner needle distal end 532 may be rounded and/or blunted to prevent inner needle 530 from poking through plug 540 and into the target tissue site and potentially injuring a patient and/or making it harder to deposit plug 540 in the target tissue site. Inner needle 530 may also include a shape memory material that may contract when exposed to body temperatures. As a result of the contraction of the shape memory material, inner needle 530 may separate from plug 540, thus making the removal of inner needle 530 easier. Inner needle 530 may also have a disk 550 with an opening 551, axially aligned with and slidably positioned around and near distal end 532 of inner needle 530. In general, disk 550 may be positioned on inner needle 530 close to a proximal end of plug 540 and disk 550 may have an outer diameter that is less than an inner diameter of outer needle 520 but greater than an inner diameter of opening 528 of tip 524. Disk 550 may be made of a semi-rigid material that may be partially compressible.

In general, in FIG. 5, the diameter of the outer needle lumen of outer needle 520 may be significantly larger than an outer diameter of inner needle 530 to permit inner needle 530, plug 540 and disk 550 to travel through the inner lumen of outer needle 520 when plug 540 is covering distal end 532 of inner needle 530. In general, the distance between the outer needle lumen of outer needle 520 and an exterior surface 542 of plug 540 may need to vary to accommodate the size and tackiness of different plugs 540. However, a benefit realized from disk 550 being slidably positioned around inner needle 530 is that disk 550 may help guide inner needle 530 through outer needle inner lumen 513, which may protect plug 540 from being damaged or knocked off inner needle 530. As a result, inner needle 530 may be easily inserted into and removed from outer needle 520, which may permit inner needle 530 to be inserted into outer needle 520 after catheter 510 has been inserted into a patient's body. In fact, inner needle 530 may be inserted into outer needle 520 after outer needle 520 has been ejected into the target tissue site and then removed from outer needle 520 after delivering the plug to the target tissue site. Unfortunately, unlike in FIG. 4 where only a new inner needle is introduced, in the embodiment in FIG. 5, new outer and inner needles 520, 530 would both need to be introduced due to the stopper effect disk 550 has in tip 528 (see description below). This may enable the repositioning of catheter 510 within the patient's body to introduce additional plugs 540 on new outer and inner needles 520, 530 into the target tissue site without having to remove catheter 510.

In FIG. 5, plug 540 may have a low profile that upon injection into tissue may activate and swell and/or expand against the tissue. The swelling and/or expansion of plug 540 may help to hold plug 540 in the tissue while inner needle 530 may be retracted back into outer needle 520. Alternatively, plug 540 may have a higher affinity for the tissue than for inner needle 530 so that when inner needle 530 is retracted out of plug 540 back into outer needle 520, plug 540 may remain in the tissue. In addition, disk 550 may act as a scraper to push plug 540 off inner needle 530 as inner needle 530 is retracted back through disk 550.

In FIG. 5, plug 540 may have a low profile that upon injection into tissue may activate and swell and/or expand against the tissue. The swelling and/or expansion of plug 540 may help to hold plug 540 in the tissue while inner needle 530 may be retracted back into outer needle 520. Alternatively, plug 540 may have a higher affinity for the tissue than for inner needle 530 so that when inner needle 530 is retracted out of plug 540 back into outer needle 520, plug 540 may remain in the tissue. In addition, disk 550 may act as scraper to push plug 540 off inner needle 530 as inner needle 530 is retracted back through disk 550. Accordingly, the medical device may incorporate means for pushing the plug off the inner member (e.g., inner needle 520) as the inner member is retracted, the pushing means being in the form of a scraper such as disk 550.

In accordance with another embodiment of the present invention, inner needle 530 of FIG. 5 may also have an inner needle lumen 535 that may extend between the inner needle proximal end 531 and inner needle distal end 532 through which a fluid may travel and an inner needle opening (not shown) defined by inner needle distal end 532 to eject the fluid. The inner needle opening may permit the injection of fluid, for example, therapeutics, drugs, etc., into plug 540 either pre- or post-implant injection of plug 540 into the tissue.

Alternatively, in FIG. 5, if inner needle 530 is hollow but closed at both ends, inner needle lumen 535 may exist although not be accessible. However, if inner needle 530 is solid, inner needle lumen 535 may not be present. For example, the fluid that may be ejected from inner needle 530 may include a therapeutic agent, a cell therapy, a crosslinker, a second component of a two-component system to create a solid plug in vivo when the plug includes a first component of the two-component system, gene therapies, drugs, proteins, and extracellular matrices. In general, and regardless of whether there is an opening at inner needle distal end 532, inner needle distal end 532 may have a blunted end to prevent inner needle 530 from poking through plug 540 and into the target tissue site and potentially injuring the patient and making it harder to deposit plug 540 in the target tissue site.

In FIG. 5, although not shown for ease of illustration, positioning and removing method elements discussed below are identical to method positioning (A) and removing (E) elements from FIG. 4. Specifically, as in FIG. 4, in FIG. 5, the method may include positioning (not shown, but same as (A) in FIG. 4) catheter distal end 512 at injection site 515, for example, a target tissue injection site, in myocardium tissue section 500, so that catheter distal end 512 abuts injection site 515. The method may also include ejecting (B') outer needle 520 and inner needle 530 with a disk 550 axially aligned with and surrounding inner needle 520 near the distal end of inner needle 520 and substantially immediately proximal to plug 540 located at inner needle distal end 532 into injection site 515 either substantially simultaneously or one at a time. In general, outer needle 520 is injected into injection site 515 before inner needle 530 and plug 540, since outer needle 520 has a sharp tip to puncture tissue and needle 530 and plug 540 do not. Specifically, outer needle 520 may be ejected from catheter 510 into injection site 515 separate from or substantially simultaneously with inner needle 530. If outer needle 520 and inner needle 530 are ejected together, inner needle 530 may be recessed within outer needle 530 to permit outer needle 530 to puncture injection site 515. The method may further include retracting (C') outer needle 520 from injection site 515 and back into catheter 510 while leaving inner needle 530 and plug 540 in injection site 515. This may also cause disk 550 to become lodged against an inner surface of wall 526 of tip 524 just proximal to opening 529. The method may still further include retracting (D') inner needle 530 from injection site 515 and back through disk 550 and into catheter 510 and outer needle 530 while leaving plug 540 in injection site 515. Disk 550 may remain lodged in tip 524 due a greater affinity between disk 550 and tip 524 than between disk 550 and inner needle 530. The method may finally include removing (not shown, but identical to (E) in FIG. 4) catheter 510 from injection site 515 with plug 540 embedded in injection site 515.

Figure 6:
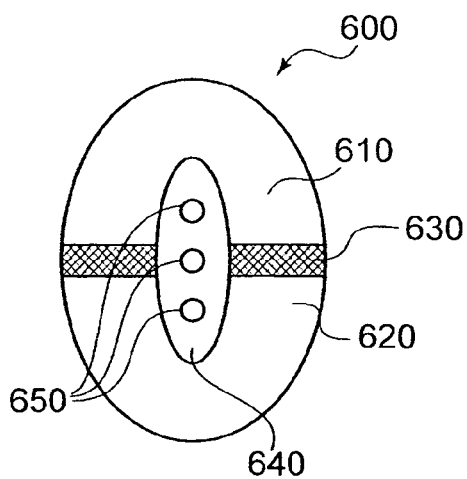
FIG. 6 is a front-end view of a distal end of a catheter with sensing electrodes, in accordance with yet another embodiment of the present invention.

FIG. 6 is a front-end view of a distal end of a catheter with sensing electrodes, in accordance with another embodiment of the present invention. In FIG. 6, a sensor 600 may include a first electrode 610 and a second electrode 620 with an insulator 630 between them to form a generally oval shape. In addition, an opening 640 may be located in sensor 600 and may be of a generally oval shape to permit one or more needles 650 to be introduced through opening 640. For example, in the embodiment of the present invention shown in FIG. 6, opening 640 may be substantially axially aligned with the center of sensor 600 and may accommodate multiple, for example, three, needles 650. However, alternative embodiments are contemplated in which less than three as well as more than three needles may be used. Regardless of the number of needles, in accordance with embodiments of the present invention, this and all multiple lumen, for example, needle and/or needle-less, designs may be used to polymerize two or more therapeutic agents upon injection. This may be accomplished by keeping each of the therapeutic agents from mixing until they are injected and/or delivered to the tissue. In the needle-less embodiments, the therapeutic may be delivered to but not injected into the target tissue. Alternative shapes are contemplated including, for example, circular and/or square.

Figure 7:
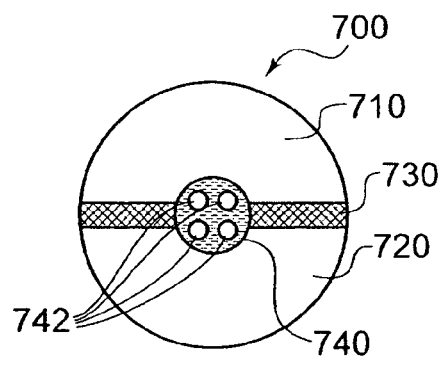
FIG. 7 is a front-end view of an alternative distal end configuration of a catheter with sensing electrodes, in accordance with yet another embodiment of the present invention.

FIG. 7 is a front-end view of an alternative distal end configuration of a catheter with sensing electrodes, in accordance with yet another embodiment of the present invention. In FIG. 7, a sensor 700 may include a first electrode 710 and a second electrode 720 separated and possibly fixed together by an insulator 730 to form a generally circular shape. In addition, an opening 740 may be located substantially axially aligned with a center of sensor 700, may be of a generally circular shape and may be substantially filled with insulator 730 in which one or more openings 742 may be placed to permit one or more needles (not shown) to be introduced through one or more openings 742. Insulator 730 may not only insulate any needles that may pass through one or more openings 742, but also may provide one or more guides and added stability for the needles. For example, in the embodiment of the present invention shown in FIG. 7, sensor 600 may accommodate up to four needles. However, other embodiments are contemplated in which less than four as well as more than four openings may be disposed in the sensor. Alternative shapes are contemplated including, for example, oval and/or square.

Figure 8:
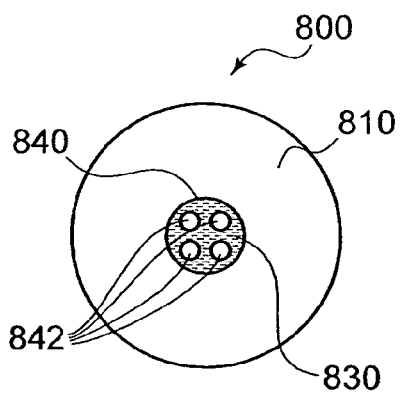
FIG. 8 is a front-end view of an alternative distal end configuration of a catheter with sensing electrodes, in accordance with yet another embodiment of the present invention.

FIG. 8 is a front-end view of an alternative distal end configuration of a catheter with sensing electrodes, in accordance with yet another embodiment of the present invention. In FIG. 8, a sensor 800 may include a single electrode 810, with an insulator 830 disposed in an opening 840 in single electrode 810. Single electrode 810 may be in a generally circular shape, and opening 840 also may be of a generally circular shape and may be located substantially axially aligned with a center of single electrode 810. In addition, insulator 830 may include one or more openings 842 to permit one or more needles (not shown) to be introduced through one or more openings 842. Insulator 830 may not only insulate any needles that may pass through the one or more openings 842, but may also provide one or more guides and added stability for the needles. For example, in the embodiment of the present invention shown in FIG. 8, sensor 800 may accommodate up to four needles and/or micro-needles. However, alternative embodiments are contemplated in which less than four as well as more than four openings may be disposed in sensor. Alternative shapes are contemplated, including, for example, oval and/or circular.

Figure 9:
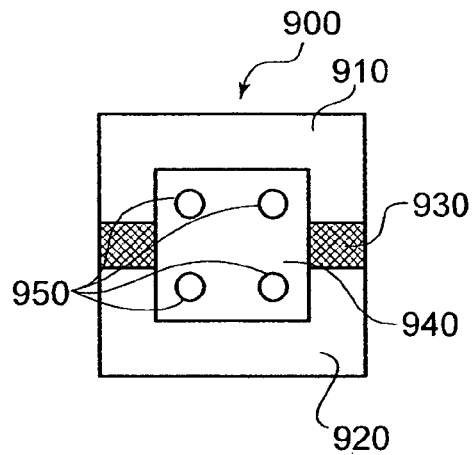
FIG. 9 is a front-end view of an alternative distal end configuration of a catheter with sensing electrodes, in accordance with yet another embodiment of the present invention.

FIG. 9 is a front-end view of an alternative distal end configuration of a catheter with sensing electrodes, in accordance with yet another embodiment of the present invention. In FIG. 9, a sensor 900 may include a first electrode 910 and a second electrode 920 fixed together by an insulator 930 to form a generally square shape. In addition, an opening 940 in sensor 900 may be of a generally square shape to permit one or more needles to be introduced through opening 940. For example, in the embodiment of the present invention shown in FIG. 9, four needles 950 are shown. However, alternative embodiments are contemplated in which less than four as well as more than four needles may be used. In another embodiment of the present invention, sensor 900 may include a substantially square shape with rounded corners and/or edges to permit easier movement into and out of a patient's body. Alternative shapes are contemplated including, for example, oval and/or square.

Figure 10:
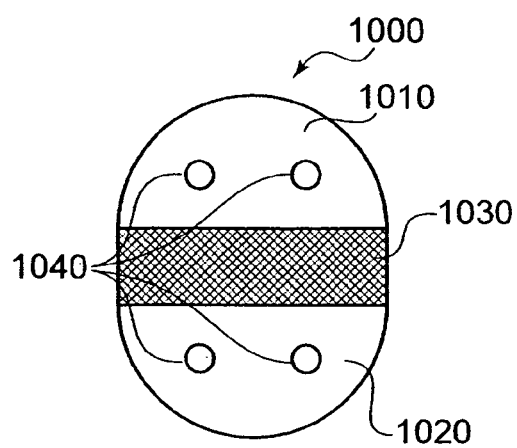
FIG. 10 is a front-end view of an alternative distal end configuration of a catheter with sensing electrodes, in accordance with yet another embodiment of the present invention.

FIG. 10 is a front-end view of an alternative distal end configuration of a catheter with sensing electrodes, in accordance with another embodiment of the present invention. In FIG. 10, a sensor 1000 may include a first electrode 1010 and a second electrode 1020 separated and possibly fixed together by an insulator 1030 running therebetween to form a substantially oval shape. In addition, one or more openings 1040 may be located in first electrode 1010 and/or second electrode 1020 to permit one or more needles to be introduced through one or more openings 1040. In this embodiment, insulator 1030 may insulate only first electrode 1010 and second electrode 1020 from each other. Any needles that pass through the one or more openings 1040 may be non-conductive or, alternatively, may be further insulated from first and/or second electrodes 1010, 1020 by an insulating coating that may be applied to the interior walls defining each of one or more openings 1040 or to the needles. One or more openings 1040 may also provide added stability for any needles that may pass through the one or more openings 1040. For example, in the embodiment of the present invention shown in FIG. 10, sensor 1000 may accommodate up to four needles. However, other embodiments are contemplated in which less than four as well as more than four openings may be disposed in the sensor. In other embodiments of the present invention, one or more openings 1040 may be disposed in insulator 1030 and/or any combination of one or more openings 1040 in electrodes 1010, 1020 and insulator 1030. Alternative shapes are contemplated, including, for example, circular, oval and/or square.

Figure 11:
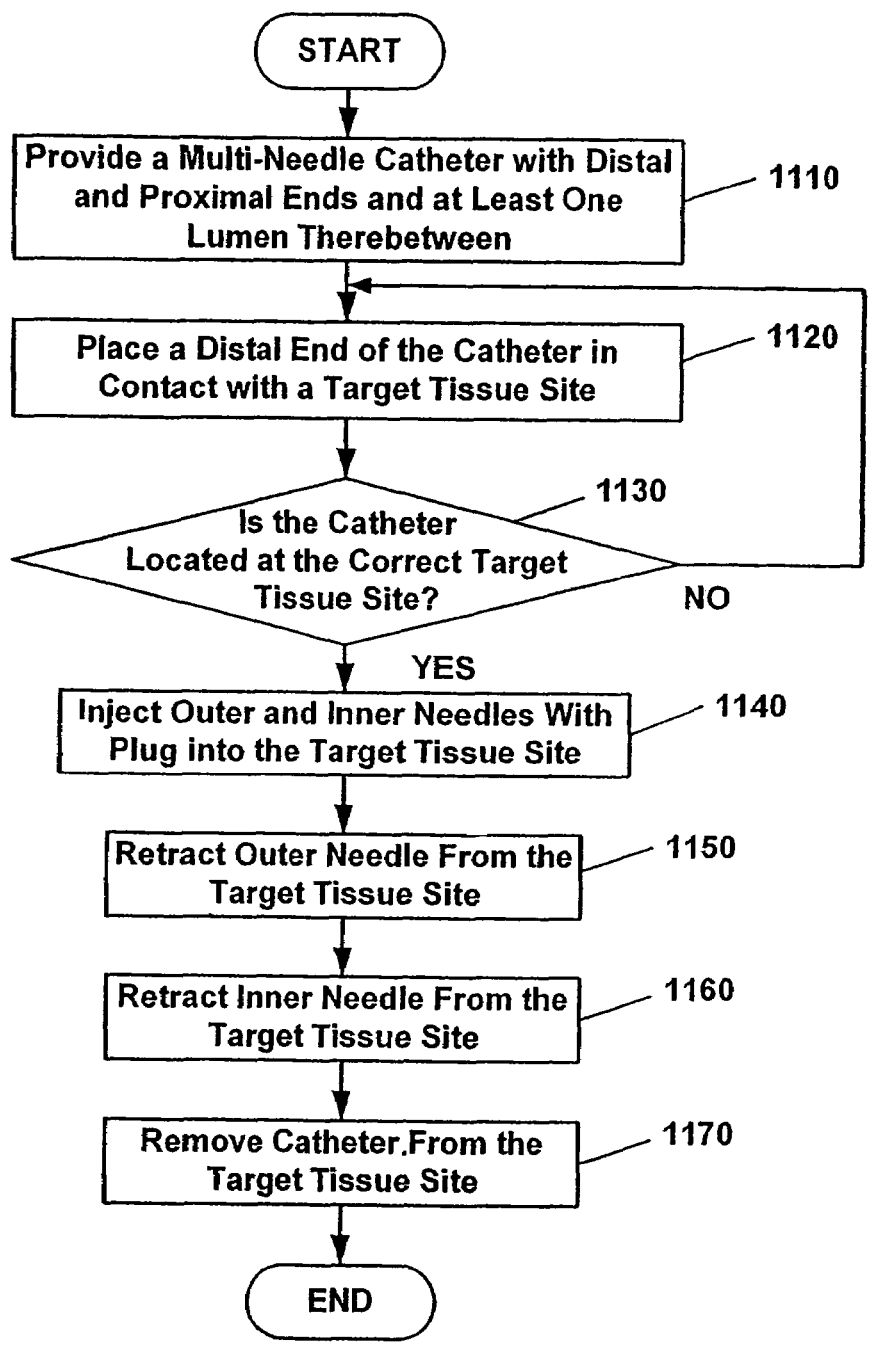
FIG. 11 is a flow diagram of a method for performing a multi-needle catheter-based injection of a plug into a target tissue site, in accordance with an embodiment of the present invention.

FIG. 11 is a flow diagram of a method for performing a multi-needle catheter-based injection of a plug, in accordance with an embodiment of the present invention. In FIG. 11, the method may include providing (1110) a multi-needle catheter with a distal end and a proximal end and at least one lumen extending therebetween. The method may also include placing (1120) the distal end of the multi-needle catheter in contact with a target site within a patient's body. The method may further include determining (1130) whether the catheter is located at the correct/desired target tissue site. If it is determined (1130) that the catheter is not located at the correct target tissue site, the method may loop back and place (1120) the distal end of the multi-needle catheter in contact with a new target site within the patient's body and continue as described above. However, if it is determined (1130) that the catheter is located at the correct target tissue site, the method may eject an outer needle and an inner needle with a plug surrounding its distal end from the catheter and inject (1140) the outer and inner needles and plug into the target tissue site. The method may include retracting (1150) the outer needle from the target tissue site and back into the catheter, while leaving the inner needle and plug embedded in the target tissue site. The method may further include retracting (1160) the inner needle from the target tissue site and back into the catheter and outer needle, while leaving the plug embedded in the target tissue site. The method may still further include removing (1170) the catheter from the target tissue site and the method may end.

Embodiments of the method of FIG. 11 are contemplated in which they may be performed using catheters equipped either with or without sensors and either with or without a deflectable tip. A detailed description of embodiments of catheter assemblies that may be used in embodiments of the present invention may be found in co-pending U.S. patent application Ser. No. 09/635,083, filed by the same assignee on Aug. 8, 2000 and entitled "Catheter Shaft Assembly," which is hereby incorporated by reference in its entirety. A detailed description of embodiments of sensor-guide catheter assemblies that may be used in embodiments of the present invention may be found in co-pending U.S. Patent Application Ser. No. 60/556,059, filed by the same assignee on Mar. 25, 2004 and entitled "Catheter With Sensor Tip and Method of Use of Same," which is hereby incorporated by reference in its entirety. A more detailed description of the operation of a deflectable tip catheter and a control assembly may be found in U.S. Pat. No. 6,083,222, issued on Jul. 4, 2000 and entitled "Deflectable Catheter for Ablating Cardiac Tissue," which is hereby incorporated by reference in its entirety.

Figure 12:
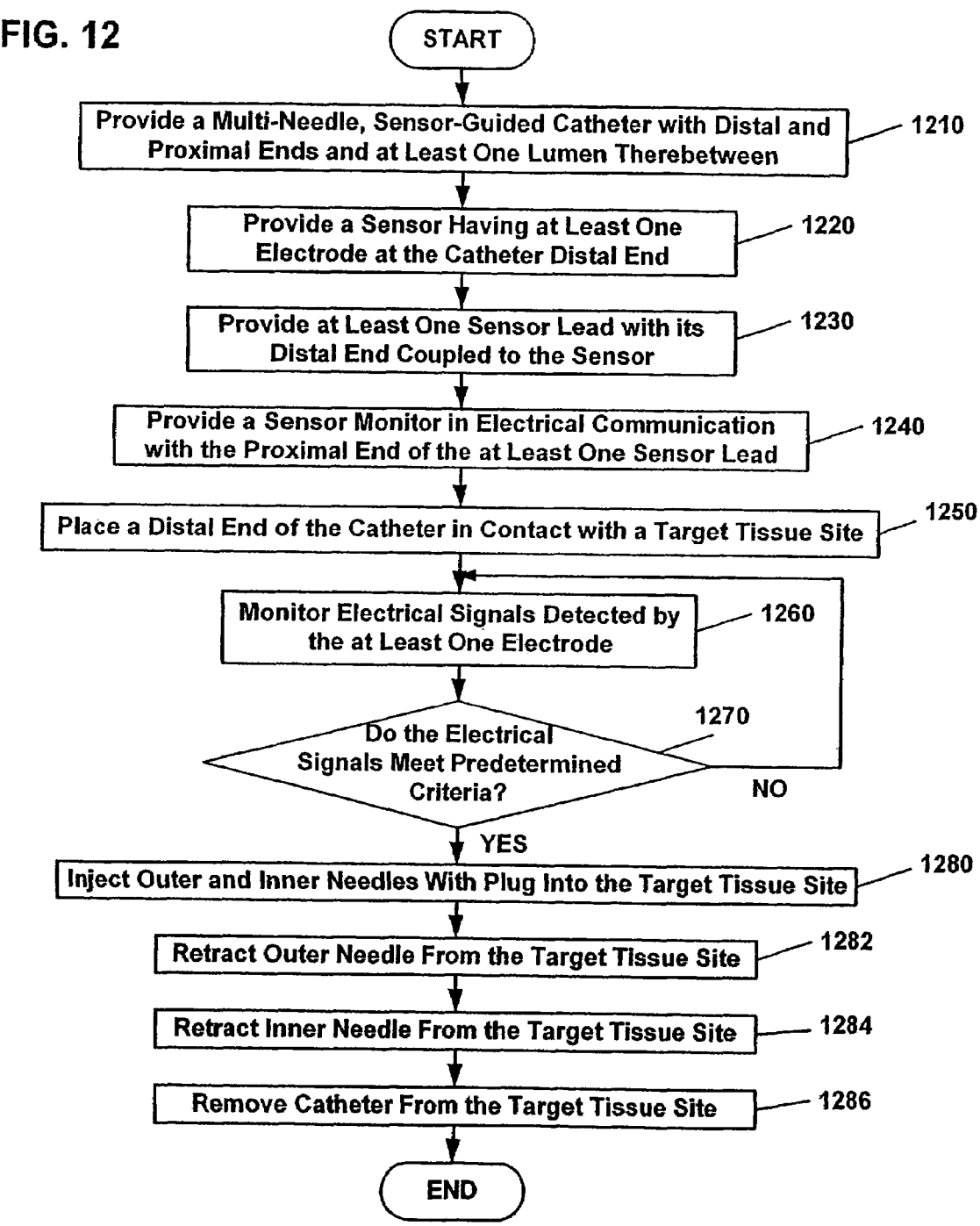
FIG. 12 is a flow diagram for performing a multi-needle catheter-based injection of a plug using a sensor-guided catheter, in accordance with an embodiment of the present invention.

FIG. 12 is a flow diagram of a method for performing a multi-needle catheter-based injection of a plug using a sensor-guided catheter, in accordance with another embodiment of the present invention. In FIG. 12, the method may include providing (1210) a multi-needle, sensor-guided catheter with a distal end and a proximal end and at least one lumen extending therebetween. The method may also include providing (1220) a sensor located at the catheter distal end, the sensor including at least one electrode, the electrode being located at the catheter distal end such that the electrode may contact a target site when the catheter distal end is placed at the target site. The sensor may also include at least two electrodes and an insulator to electrically insulate the at least two electrodes from one another. The needles may be electrically insulated from the at least one electrode. The method may include providing (1230) at least one sensor lead, a distal end of each at least one sensor lead may be in electrical communication with a corresponding sensor, and a proximal end of each at least one sensor lead may extend to the catheter proximal end. The method may also include providing (1240) a sensor monitor in electrical communication with the proximal end(s) of the at least one sensor lead to monitor electrical signals from the at least one electrode. The method may further include placing (1250) a distal end of the catheter in contact with a target site within a patient's body. The method may still further include monitoring (1260) electrical signals detected by the electrode(s) and determining (1270) whether the electrical signals detected by the electrode(s) meet a predetermined injection criteria. The method may continue monitoring (1260) the electrical signals, if the electrical signals are determined (1270) to not meet the predetermined injection criteria. However, if it is determined (1270) that the electrical signals meet the predetermined injection criteria, the method may eject an outer needle and an inner needle with a plug surrounding its distal end from the catheter and inject (1280) the outer and inner needles and plug into the target tissue site. The method may include retracting (1282) the outer needle from the target tissue site and back into the catheter, while leaving the inner needle and plug embedded in the target tissue site. The method may further include retracting (1284) the inner needle from the target tissue site and back into the catheter and outer needle, while leaving the plug embedded in the target tissue site. The method may still further include removing (1286) the catheter from the target tissue site and the method may end.

The term "therapeutic agent" as used herein may include one or more "therapeutic agents" or "drugs." The terms "therapeutic agents" and "drugs" are used interchangeably herein and may include pharmaceutically active compounds, nucleic acids with and without carrier vectors such as lipids, compacting agents (such as histones), viruses (such as adenovirus, andenoassociated virus, retrovirus, lentivirus and α-virus), polymers, hyaluronic acid, proteins, cells and the like, with or without targeting sequences.

Specific examples of therapeutic agents used in conjunction with the present invention may include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral liposomes, and cationic and anionic polymers, and neutral polymers, that are selected from a number of types depending on the desired application. Non-limiting examples of virus vectors or vectors derived from viral sources may include adenoviral vectors, herpes simplex vectors, papilloma vectors, adeno-associated vectors, retroviral vectors, and the like. Non-limiting examples of biologically active solutes may include anti-thrombogenic agents such as heparin, heparin derivatives, urokinase, and PPACK (dextrophenylalanine proline arginine chloromethyl ketone); antioxidants such as probucol and retinoic acid; angiogenic and anti-angiogenic agents and factors; anti-proliferative agents such as enoxaprin, angiopeptin, rapamycin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as lisidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells may be of human origin (autologous or allogeneic) or may be from an animal source (xenogeneic), genetically engineered if desired to deliver proteins of interest at the insertion site. Any modifications are routinely made by one skilled in the art.

Polynucleotide sequences useful in practice of the invention may include DNA or RNA sequences having a therapeutic effect after being taken up by a cell. Examples of therapeutic polynucleotides may include anti-sense DNA and RNA; DNA coding for an anti-sense RNA; or DNA coding for tRNA or rRNA to replace defective or deficient endogenous molecules. The polynucleotides may also code for therapeutic proteins or polypeptides. A polypeptide is understood to be any translation product of a polynucleotide regardless of size, and whether glycosylated or not. Therapeutic proteins and polypeptides may include as a primary example, those proteins or polypeptides that can compensate for defective or deficient species in an animal, or those that act through toxic effects to limit or remove harmful cells from the body. In addition, the polypeptides or proteins that may be injected, or whose DNA can be incorporated, may include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin-like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which may be provided as polypeptides or as DNA encoding these polypeptides, include monocyte chemoattractant protein ("MCP-1"), and the family of bone morphogenic proteins ("BMPs"). The known proteins may include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMPs are any of BMP-2, BMP-3, BMP-4, BMP-5, BMP-6 and BMP-7. These dimeric proteins may be provided as homodimers, heterodimers, or combinations thereof, alone or together with other molecules. Alternatively or, in addition, molecules capable of inducing an upstream or downstream effect of a BMP may be provided. Such molecules may include any of the "hedgehog" proteins, or the DNAs encoding them.

Although the present invention has been disclosed in detail, it should be understood that various changes, substitutions, and alterations may be made herein, the present invention is intended to cover various modifications and equivalent arrangements. Other examples are readily ascertainable from the above description by one skilled in the art and may be made without departing from the spirit and scope of the present invention as defined by the following claims.

What is claimed is:

1. A medical device, comprising:
    a catheter with a distal end and a proximal end and a catheter lumen extending therebetween;
    an outer needle with a distal end and a proximal end and an outer needle lumen extending therebetween, the outer needle being disposed in the catheter lumen, the outer needle slidable within the catheter;
    an inner needle with a distal end and a proximal end, the inner needle being disposed in the outer needle lumen, a therapeutic plug positioned on the distal end of the inner needle, the plug positioned between an outer wall of the inner needle and an inner wall of the outer needle, the outer wall of the inner needle being spaced apart from the inner wall of the outer needle;
    a needle control mechanism coupled to the proximal ends of the outer needle and the inner needle, the needle control mechanism configured to control the ejection and retraction of the outer and inner needles to deliver a therapeutic plug into a target tissue site; and
    a disk with an opening, axially aligned with and slidably positioned around the distal end of the inner needle with the inner needle projecting through the disk and the disk positioned proximal to the plug, the disk being located within the outer needle, the disk adapted to push the plug off the inner needle as the inner needle is retracted through the disk.

2. The medical device of claim 1, wherein the needle control mechanism comprises:
    an actuator to eject the distal ends of the outer and inner needles past the distal end of the catheter on a first actuation of the actuator, the actuator to retract the distal end of the outer needle into the distal end of the catheter on a second actuation of the actuator, and the actuator to retract the distal end of the inner needle into the distal end of the catheter on a third actuation of the actuator.

3. The medical device of claim 1, wherein the needle control mechanism comprises:
    a first actuator to simultaneously control the ejection and retraction of the outer needle and the inner needle;
    a second actuator to control the ejection and retraction of the outer needle; and
    a third actuator to control the ejection and retraction of the inner needle.

4. The medical device of claim 1, wherein the outer needle comprises:
    a needle tip at the distal end of the outer needle.

5. The medical device of claim 4, wherein the inner needle has an inner needle lumen extending between the distal end and the proximal end to deliver an agent at the distal end.

6. The medical device of claim 5, wherein the agent comprises one of a therapeutic agent and a cell therapy.

7. The medical device of claim 5, wherein the agent comprises one of a cross-linker and a second component of a two component system to solidify the plug in the target tissue site.

8. The medical device of claim 4, wherein the inner needle comprises a shape memory material that contracts away from the plug at body temperature.

9. The medical device of claim 4, wherein the therapeutic plug swells upon injection into the target tissue site to be held in the target tissue site.

10. The medical device of claim 4, wherein the needle tip has a substantially symmetrically tapered portion defining a needle tip inner opening to the outer needle lumen at a distal end of the needle tip, the needle tip inner opening having a diameter less than the substantially constant cylindrical inner diameter of the outer needle.

11. The medical device of claim 10, wherein the substantially constant cylindrical diameter of the outer needle is greater than an outer diameter of the disk.

12. The medical device of claim 11, wherein the outer diameter of the disk is to fit tightly within the diameter of the needle tip inner opening to permit the retraction of the inner needle from the disk.

13. The medical device of claim 12, wherein the outer diameter of the disk is compressed at the diameter of the needle tip inner opening.

14. The medical device of claim 1 wherein the outer needle has a rim with a distally facing cutting edge.

15. The medical device of claim 1 wherein the outer needle has a tapered end sized to prevent travel of the disc from within the outer needle to out of the tapered end.

16. The medical device of claim 1 wherein the disc has a diameter, and wherein the outer lumen has a first section and a second section, the first section having a radius along its longitudinal axis smaller than a diameter of the disc, the second section having a radius along its longitudinal axis larger than the diameter of the disc.

17. The medical device of claim 1 wherein the inner needle comprises a block copolymer of caprolactone and dioxanone.

18. . A medical device comprising:
a therapeutic plug;
a catheter surrounding the therapeutic plug;
an outer lumen slidable within the catheter and surrounding the therapeutic plug, the outer lumen having a distal end extendible beyond a distal end of the catheter, the outer lumen having a piercing end;
an inner longitudinal member, the inner longitudinal member slidably positioned within the outer lumen, an end of the inner member positioned within the therapeutic plug such that the plug is separable from the inner member, the end having a blunted tip, the distal end of the outer lumen extendible beyond the therapeutic plug when the inner member is positioned within the therapeutic plug;
means for pushing the plug off the inner member as the inner member is retracted, said pushing means being positioned around the inner member with the inner member projecting through said pushing means; and
an actuator at a proximal end of the outer lumen of the inner longitudinal member, the actuator configured to activate relative movement between the outer lumen and the inner longitudinal member, wherein when the inner member is retracted by the actuator, the therapeutic plug is separated from the inner member.

19. The medical device of claim 18 further comprising a sensor within the catheter, the sensor having a first electrode, a second electrode and two or more needle openings.

20. A medical device, comprising:
a therapeutic plug;
a catheter with a distal end and a proximal end and a catheter lumen extending therebetween, the therapeutic plug positioned within the catheter lumen;
an outer needle with a distal end and a proximal end and an outer needle lumen extending therebetween, the outer needle being disposed in the catheter lumen;
an inner needle with a distal end and a proximal end, the inner needle being disposed in the outer needle lumen and the distal end of the inner needle positioned within the therapeutic plug, the inner needle slidable within the outer needle, the therapeutic plug positioned between an outer surface of the inner needle and an inner surface of the outer needle, the therapeutic plug releaseably positioned around the inner needle;
means for pushing the plug off the inner needle as the inner needle is retracted, said pushing means being positioned around the inner needle with the inner needle projecting through said pushing means; and
a means for needle control coupled to the proximal ends of the outer needle and the inner needle, the needle control means controlling the independent and joint ejection and retraction of the outer and inner needles to deliver the therapeutic plug to a target tissue site.

* * * * *